(12) United States Patent
Terui et al.

(10) Patent No.: US 11,047,994 B2
(45) Date of Patent: Jun. 29, 2021

(54) RADIATION IMAGING APPARATUS

(71) Applicant: CANON KABUSHIKI KAISHA, Tokyo (JP)

(72) Inventors: Kosuke Terui, Yokohama (JP); Atsushi Iwashita, Tokyo (JP); Akira Tsukuda, Kawasaki (JP); Sota Torii, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/731,143

(22) Filed: Dec. 31, 2019

(65) Prior Publication Data

US 2020/0150286 A1 May 14, 2020

Related U.S. Application Data

(63) Continuation of application No. PCT/JP2018/027533, filed on Jul. 23, 2018.

(30) Foreign Application Priority Data

Jul. 28, 2017 (JP) .............................. JP2017-146801

(51) Int. Cl.
  *H01L 27/146* (2006.01)
  *G01T 1/17* (2006.01)
  *G01T 1/29* (2006.01)

(52) U.S. Cl.
  CPC .............. *G01T 1/17* (2013.01); *G01T 1/2928* (2013.01); *H01L 27/14663* (2013.01)

(58) Field of Classification Search
  CPC ... G01T 1/17; G01T 1/2928; H01L 27/14663; H04N 5/378; H04N 5/37452;
  (Continued)

(56) References Cited

U.S. PATENT DOCUMENTS 7,227,926 B2  6/2007  Kameshima et al.
9,048,154 B2  6/2015  Takenaka et al.
(Continued)

FOREIGN PATENT DOCUMENTS

DE  3030093 A1  3/1982
EP  2649941 A1  10/2013
(Continued)

*Primary Examiner* — Kiho Kim
(74) *Attorney, Agent, or Firm* — Venable LLP

(57) ABSTRACT

Radiation imaging apparatus includes pixel array having pixels, readout circuit for reading signals from the pixel array, and detector for detecting, based on radiation emitted from radiation source or information provided from the radiation source, start of radiation irradiation by the radiation source, and controller for determining timing of each of operations of sample and hold in each of the pixels each time the start of radiation irradiation is detected by the detector. The timing of at least one operation of the operations is timing in radiation irradiation period, and each of the pixels includes convertor for converting radiation into electrical signal, and sample and hold circuit for sample-holding the signal from the conversion element over plural times in accordance with the timing of each of the operations determined by the controller.

16 Claims, 12 Drawing Sheets

(58) Field of Classification Search
CPC .... H04N 5/3205; A61B 6/5264; A61B 6/482; A61B 6/4233; A61B 6/54
See application file for complete search history.

(56) References Cited

U.S. PATENT DOCUMENTS

| | | |
|---|---|---|
| 9,050,059 B2 | 6/2015 | Kuwabara |
| 9,128,196 B2 | 9/2015 | Sato et al. |
| 9,128,368 B2 | 9/2015 | Tajima |
| 9,134,432 B2 | 9/2015 | Iwashita et al. |
| 9,234,966 B2 | 1/2016 | Sugawara et al. |
| 9,423,512 B2 | 8/2016 | Sato et al. |
| 9,445,030 B2 | 9/2016 | Yagi et al. |
| 9,462,989 B2 | 10/2016 | Takenaka et al. |
| 9,468,414 B2 | 10/2016 | Ryu et al. |
| 9,470,800 B2 | 10/2016 | Iwashita et al. |
| 9,470,802 B2 | 10/2016 | Okada et al. |
| 9,541,653 B2 | 1/2017 | Iwashita et al. |
| 9,655,586 B2 | 5/2017 | Yagi et al. |
| 9,812,474 B2 | 11/2017 | Yagi et al. |
| 9,820,711 B2 | 11/2017 | Tsukuda |
| 9,971,046 B2 | 5/2018 | Ryu et al. |
| 9,980,685 B2 | 5/2018 | Iwashita et al. |
| 9,989,656 B2 | 6/2018 | Sato et al. |
| 10,009,990 B2 | 6/2018 | Takenaka et al. |
| 10,070,082 B2 | 9/2018 | Tsukuda |
| 10,197,684 B2 | 2/2019 | Terui et al. |
| 10,274,612 B2 | 4/2019 | Ishii et al. |
| 10,441,238 B2 | 10/2019 | Terui et al. |
| 2002/0024601 A1 | 2/2002 | Kaifu |
| 2002/0101527 A1 | 8/2002 | Endo |
| 2007/0125952 A1* | 6/2007 | Endo .................. G01T 1/17 250/369 |
| 2012/0087471 A1 | 4/2012 | Naito |
| 2012/0132825 A1* | 5/2012 | Amitani ............... A61B 6/542 250/394 |
| 2013/0082184 A1 | 4/2013 | Nakatsugawa |
| 2013/0322597 A1 | 12/2013 | Uchiyama |
| 2014/0072098 A1 | 3/2014 | Kappler |
| 2014/0112448 A1* | 4/2014 | Takenaka ............ H04N 5/3742 378/114 |
| 2014/0239186 A1 | 8/2014 | Sato et al. |
| 2014/0361189 A1 | 12/2014 | Kameshima et al. |
| 2015/0071414 A1 | 3/2015 | Oda |
| 2015/0238159 A1* | 8/2015 | Al Assad ............. A61B 6/025 378/5 |
| 2015/0296151 A1* | 10/2015 | Dowaki ............... H04N 5/343 250/370.08 |
| 2016/0131772 A1 | 5/2016 | Sato |
| 2016/0270755 A1 | 9/2016 | Takenaka et al. |
| 2018/0128755 A1 | 5/2018 | Iwashita et al. |
| 2018/0317868 A1 | 11/2018 | Terui et al. |
| 2018/0328862 A1 | 11/2018 | Sato et al. |
| 2018/0341029 A1 | 11/2018 | Iwashita et al. |
| 2019/0179036 A1 | 6/2019 | Takenaka et al. |
| 2019/0320993 A1 | 10/2019 | Noda et al. |
| 2019/0349541 A1 | 11/2019 | Iwashita et al. |
| 2020/0124749 A1 | 4/2020 | Takenaka et al. |

FOREIGN PATENT DOCUMENTS

| | | |
|---|---|---|
| EP | 3582489 A1 | 12/2019 |
| JP | 2005-287773 | 10/2005 |
| JP | 2009-504221 | 2/2009 |
| JP | 2012-125409 A | 7/2012 |
| JP | 2013-141559 | 7/2013 |
| JP | 2017-083408 | 5/2017 |
| JP | 2018-075252 | 5/2018 |
| WO | 2007/017773 | 2/2007 |
| WO | 2012/032801 | 3/2012 |
| WO | 2018/147217 A1 | 8/2018 |

\* cited by examiner

RADIATION IMAGING APPARATUS

CROSS-REFERENCE TO RELATED APPLICATIONS

This application is a Continuation of International Patent Application No. PCT/JP2018/027533, filed Jul. 23, 2018, which claims the benefit of Japanese Patent Application No. 2017-146801, filed Jul. 28, 2017, both of which are hereby incorporated by reference herein in their entirety.

BACKGROUND OF THE INVENTION

Field of the Invention

The present invention relates to a radiation imaging apparatus.

Background Art

There is an energy subtraction method as an imaging method that applies a radiation imaging apparatus. The energy subtraction method is a method of obtaining new images (for example, a bone image and a soft tissue image) by processing a plurality of images obtained by capturing an object a plurality of times while changing energy of radiation to irradiate the object. A time interval during which a plurality of radiation images are captured is, for example, several seconds or more in a radiation imaging apparatus to capture a still image, about 100 msec in a general radiation imaging apparatus for a moving image, and about 10 msec even in a radiation imaging apparatus for a high-speed moving image. If the object moves in this time interval, an artifact is caused by that movement. It is therefore difficult to obtain, by the energy subtraction method, a radiation image of an object such as a heart that moves fast.

PTL 1 describes a system that performs dual energy imaging. In this system, the tube voltage of an X-ray source is set to the first kV value, and then changed to the second kV value in imaging. Then, the first signal corresponding to the first sub-image is integrated when the tube voltage is the first kV value, and integration is reset after the integrated signal is transferred to a sample and hold node. Subsequently, the second signal corresponding to the second sub-image is integrated when the tube voltage is the second kV value. Consequently, readout of the integrated first signal and integration of the second signal are performed parallelly.

When a plurality of frames of a moving image are captured by performing X-ray exposure a plurality of times using the method described in PTL 1, the time from the X-ray exposure to the transfer of the signal to the sample and hold node can be different for each frame. Consequently, the energy and dose of the first sub-image differ between the frames, and the energy and dose of the second sub-image also differ between the frames. This can cause a decrease in accuracy of energy subtraction.

CITATION LIST

Patent Literature

PTL 1: Japanese Patent Laid-Open No. 2009-504221

SUMMARY OF THE INVENTION

The present invention provides a technique advantageous in reducing variation in time from the start of radiation irradiation to sampling and holding of a signal.

An aspect of the present invention relates to a radiation imaging apparatus comprising a pixel array including a plurality of pixels, and a readout circuit configured to read out signals from the pixel array. The radiation imaging apparatus comprises a detection unit configured to detect, based on radiation emitted from a radiation source or information provided from the radiation source, a start of irradiation of radiation by the radiation source, and a control unit configured to determine a timing of each of a plurality of sample and hold operations in each of the plurality of pixels each time the start of irradiation of radiation is detected by the detection unit, wherein the timing of at least one sample and hold operation of the plurality of sample and hold operations is a timing in a radiation irradiation period, and each of the plurality of pixels includes a conversion element configured to convert radiation into an electrical signal, and a sample and hold circuit configured to sample and hold the signal from the conversion element over a plurality of times in accordance with the timing of each of the plurality of sample and hold operations determined by the control unit.

Further features of the present invention will become apparent from the following description of exemplary embodiments with reference to the attached drawings.

DESCRIPTION OF THE EMBODIMENTS

Exemplary embodiments of the present invention will be explained below with reference to the accompanying drawings.

Figure 1:
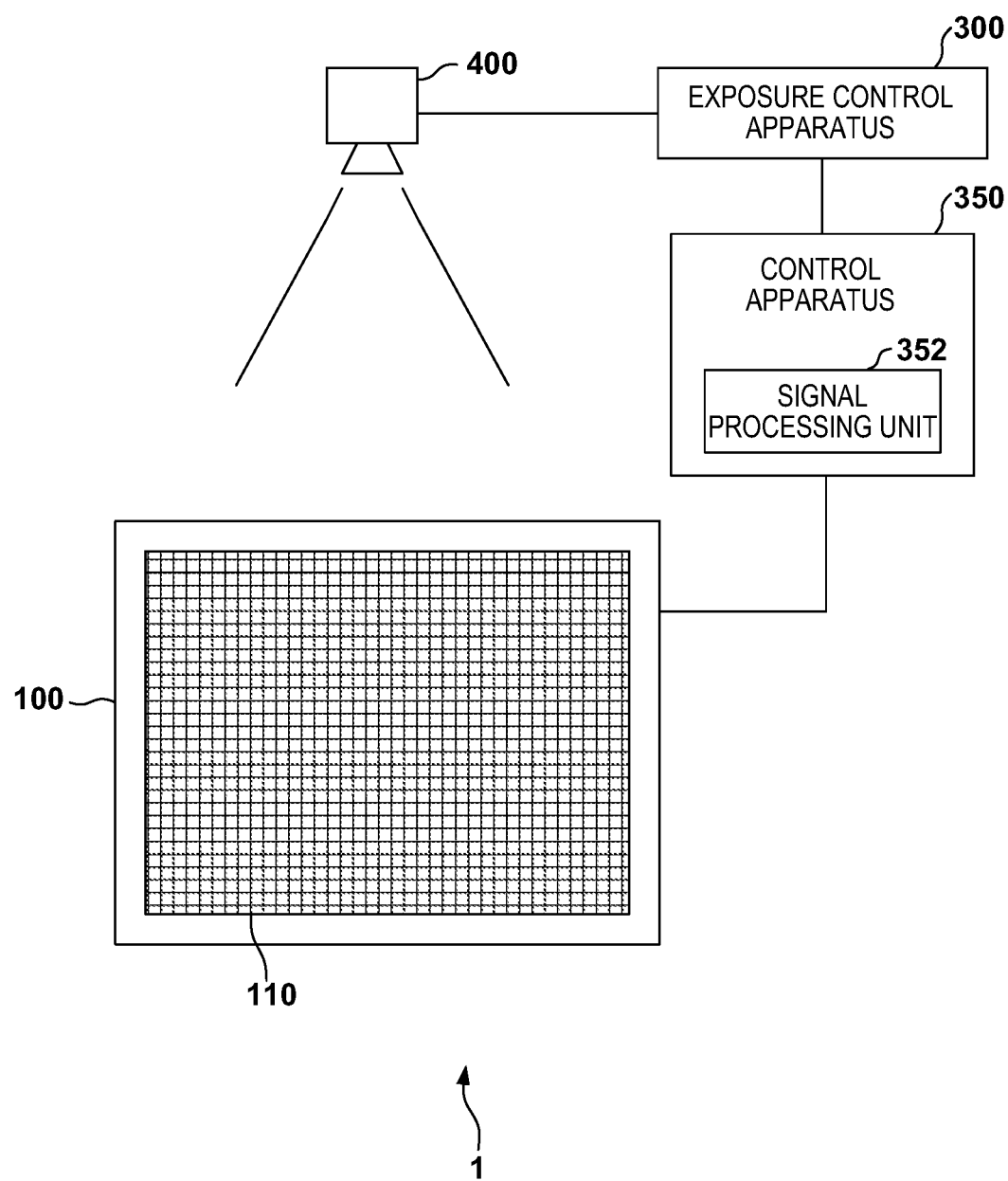
FIG. 1 is a diagram showing the arrangement of a radiation imaging apparatus according to the first embodiment of the present invention.

FIG. 1 shows the arrangement of a radiation imaging apparatus 1 according to the first embodiment of the present invention. The radiation imaging apparatus 1 can include an imaging unit 100 including a pixel array 110 including a plurality of pixels and a signal processing unit 352 that processes a signal from the imaging unit 100. The imaging unit 100 can have, for example, a panel shape. As exemplified in FIG. 1, the signal processing unit 352 may be arranged as part of a control apparatus 350, incorporated in the same housing as the imaging unit 100, or incorporated in a housing different from that of the imaging unit 100 and the control apparatus 350. The radiation imaging apparatus 1 is an apparatus for obtaining a radiation image by an energy subtraction method. The energy subtraction method is a method of obtaining new radiation images (for example, a bone image and a soft tissue image) by processing a plurality of images obtained by capturing an object a plurality of times while changing energy of radiation to irradiate the object. The term "radiation" can include, for example, α-rays, β-rays, γ-rays, particle rays, and cosmic rays in addition to X-rays.

The radiation imaging apparatus 1 can include a radiation source 400 that generates radiation, an exposure control apparatus 300 that controls the radiation source 400, and the control apparatus 350 that controls the exposure control apparatus 300 (the radiation source 400) and the imaging unit 100. As described above, the control apparatus 350 can include the signal processing unit 352 that processes a signal supplied from the imaging unit 100. All or some functions of the control apparatus 350 can be incorporated in the imaging unit 100. Alternatively, some functions of the imaging unit 100 can be incorporated in the control apparatus 350. The control apparatus 350 can be formed by a computer (processor) and a memory that stores programs provided for the computer. The signal processing unit 352 can be made of some of the programs. Alternatively, the signal processing unit 352 can be made of a computer (processor) and a memory that stores programs provided for the computer. The control apparatus 350 may be formed by a DSP (digital signal processor) or a PLA (programmable logic array) entirely or partially. The control apparatus 350 and the signal processing unit 352 may be designed and manufactured by a logic synthesis tool based on a file that describes their operations.

When permitting radiation irradiation (exposure) by the radiation source 400, the control apparatus 350 transmits an exposure permission signal to the exposure control apparatus 300. When the exposure permission signal is received from the control apparatus 350, the exposure control apparatus 300 causes the radiation source 400 to perform radiation irradiation (exposure) in response to the reception of the exposure permission signal. When capturing a moving image, the control apparatus 350 transmits an exposure permission signal to the exposure control apparatus 300 a plurality of times. In this case, the control apparatus 350 may transmit an exposure permission signal to the exposure control apparatus 300 a plurality of times at a predetermined cycle, or may transmit an exposure permission signal to the exposure control apparatus 300 each time the imaging unit 100 can capture the next frame.

The radiation source 400 can emit radiation whose energy (wavelength) changes in a continuous radiation period (irradiation period) of the radiation. By using such radiation, radiation images are obtained at a plurality of energies different from each other, and these radiation images are processed by the energy subtraction method, thereby obtaining a new radiation image.

Alternatively, the radiation source 400 may have a function of changing radiation energy (wavelength). The radiation source 400 can have a function of changing the radiation energy by changing, for example, a tube voltage (a voltage applied between the cathode and anode of the radiation source 400).

Each of the plurality of pixels forming the pixel array 110 of the imaging unit 100 includes a conversion element that converts radiation into an electrical signal (for example, charges) and a reset unit that resets the conversion element. Each pixel may be configured to convert the radiation into the electrical signal directly or may be configured to convert the radiation into light such as visible light, and then convert the light into the electrical signal. In the latter case, a scintillator for converting radiation into light can be used. The plurality of pixels that form the pixel array 110 can share the scintillator.

Figure 2:
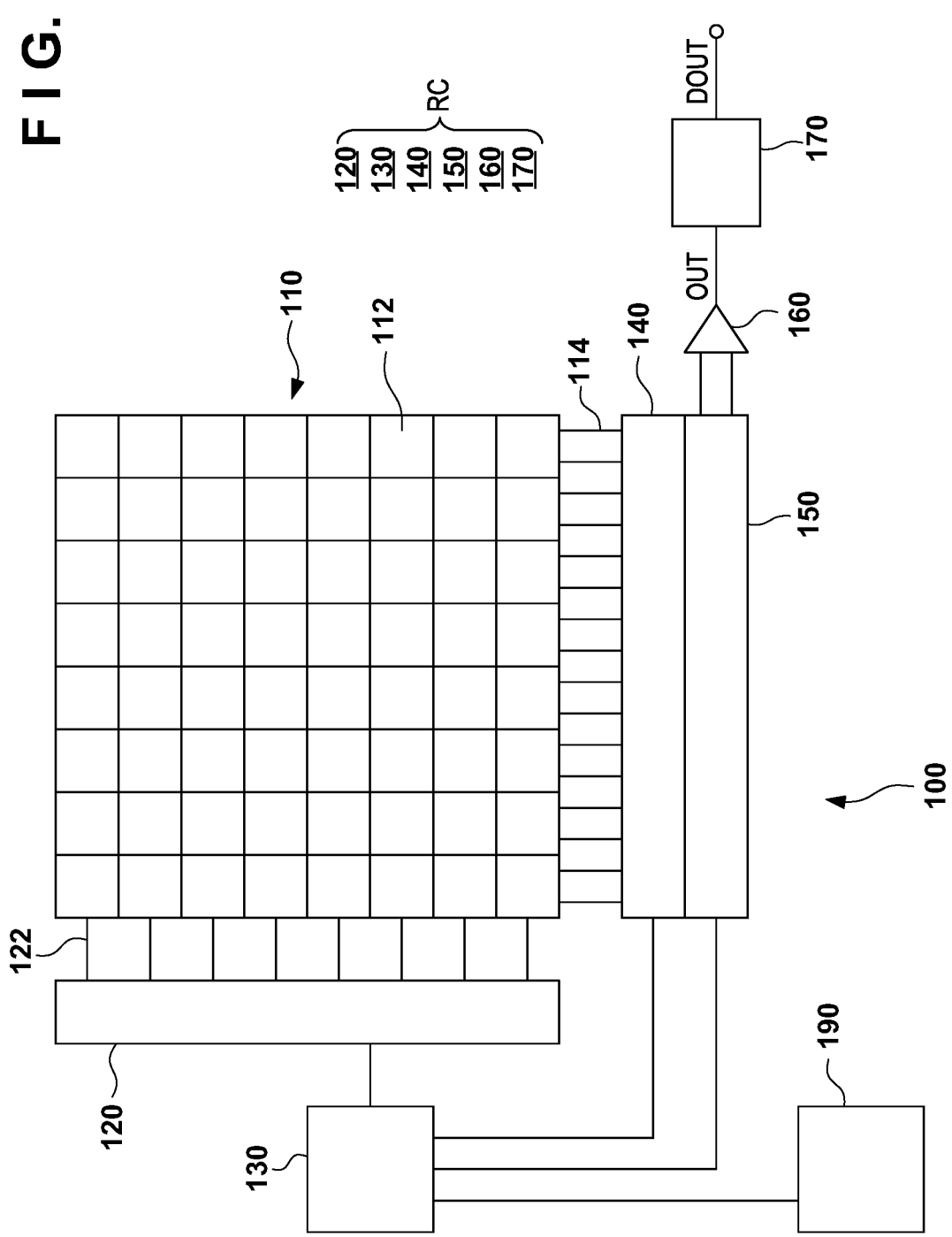
FIG. 2 is a view showing an example of the arrangement of an imaging unit.

FIG. 2 shows an example of the arrangement of the imaging unit 100. The imaging unit 100 includes the pixel array 110 including a plurality of pixels 112 and a readout circuit RC that reads out signals from the plurality of pixels 112 of the pixel array 110. The plurality of pixels 112 can be arrayed to form a plurality of rows and a plurality of columns. The readout circuit RC can include a row selection circuit 120, a control unit 130, a buffer circuit 140, a column selection circuit 150, an amplification unit 160, an AD converter 170, and a detection unit 190.

The row selection circuit 120 selects a row of the pixel array 110. The row selection circuit 120 can be arranged to select a row by driving a row control signal 122. The buffer circuit 140 buffers signals from the pixels 112 of one of the plurality of rows of the pixel array 110, which is selected by the row selection circuit 120. The buffer circuit 140 buffers the signals of a plurality of columns output to a plurality of column signal transmission paths 114 of the pixel array 110. The column signal transmission path 114 in each column includes a first column signal line and a second column signal line which form a column signal line pair. A noise level (at the time of a normal mode to be described later) of the pixel 112 or a radiation signal (at the time of an extension mode to be described later) corresponding to the radiation detected in the pixel 112 can be output to the first column signal line. A radiation signal corresponding to the radiation detected in the pixel 112 can be output to a second column signal line 322. The buffer circuit 140 can include an amplifier circuit.

The column selection circuit 150 selects, in a predetermined order, signal pairs of one row buffered by the buffer circuit 140. The amplification unit 160 amplifies the signal pairs selected by the column selection circuit 150. In this case, the amplification unit 160 can be arranged as a differential amplifier that amplifies the difference of a signal pair (two signals). The AD converter 170 can include the AD converter 170 that A/D-converts a signal OUT output from the amplification unit 160 and outputs a digital signal DOUT (a radiation image signal).

The detection unit 190 detects the start of radiation irradiation by the radiation source 400 based on the radiation emitted from the radiation source 400. The detection unit 190 can detect the start of radiation irradiation by the radiation source 400 by detecting, for example, the radiation emitted from the radiation source 400 toward the pixel array 110 based on a signal read out from the pixel array 110 by the readout circuit RC. Alternatively, the detection unit 190 can detect the start of radiation irradiation by the radiation source 400 based on a current flowing through a bias line that supplies a bias voltage to each pixel. When the start of radiation irradiation by the radiation source 400 is detected, the detection unit 190 generates a synchronization signal indicating the start and supplies it to the control unit 130.

Figure 3:
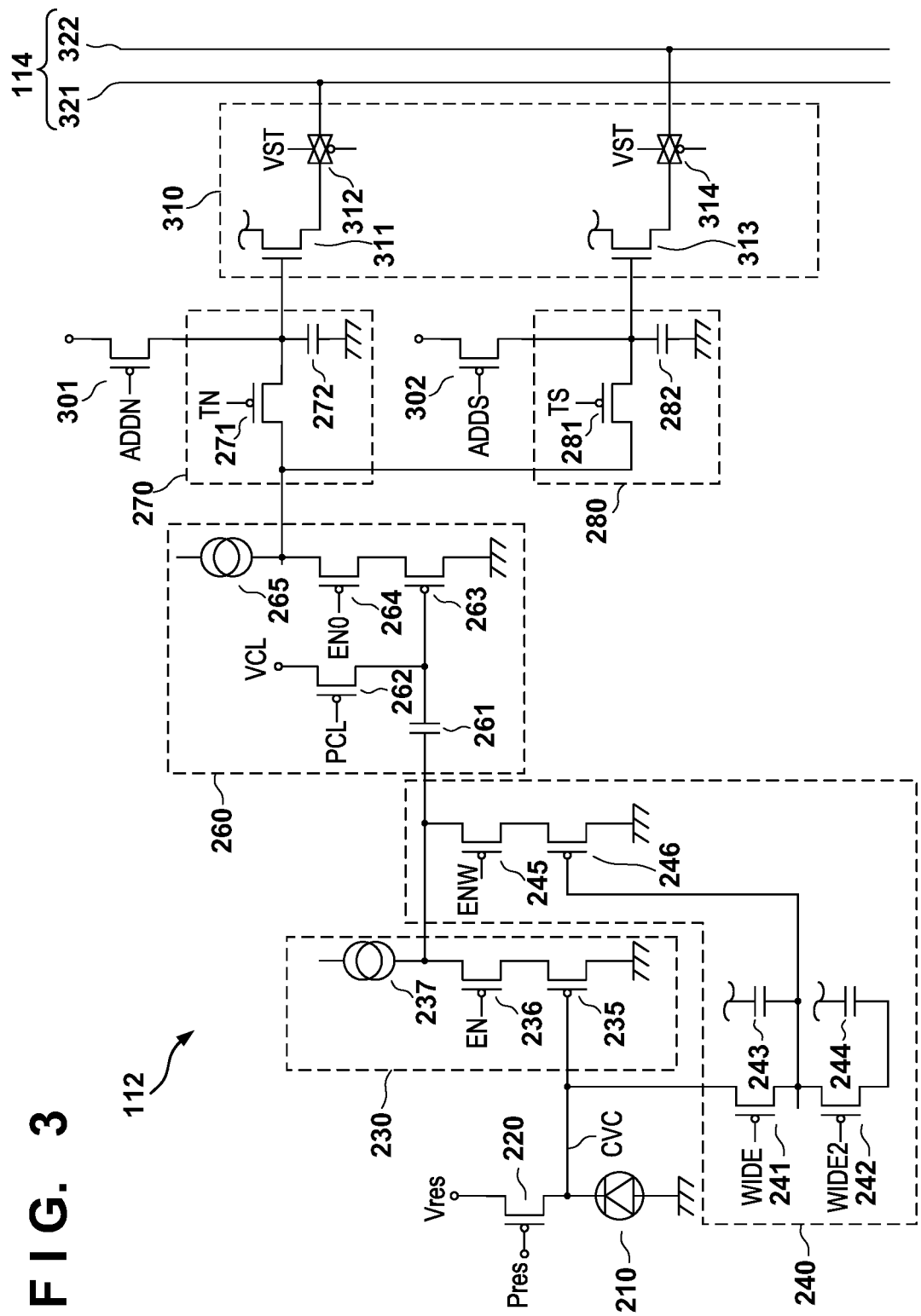
FIG. 3 is a circuit diagram showing an example of the arrangement of one pixel.

FIG. 3 shows an example of the arrangement of one pixel 112. The pixel 112 includes, for example, a conversion element 210, a reset switch 220 (reset unit), an amplifier circuit 230, a sensitivity changing unit 240, a clamp circuit 260, sample and hold circuits (holding portions) 270 and 280, and an output circuit 310. Each pixel 112 can have the normal mode and the extension mode as the modes concerning the imaging method. The extension mode is a mode for obtaining a radiation image in accordance with the energy subtraction method.

The conversion element 210 converts radiation into an electrical signal. The conversion element 210 can be formed by, for example, a scintillator that can be shared by the plurality of pixels and a photoelectric conversion element. The conversion element 210 includes a charge accumulation portion that accumulates a converted electrical signal (charges), that is, an electrical signal corresponding to radiation. The charge accumulation portion is connected to the input terminal of the amplifier circuit 230.

The amplifier circuit 230 can include MOS transistors 235 and 236, and a current source 237. The MOS transistor 235 is connected to the current source 237 via the MOS transistor 236. The MOS transistor 235 and the current source 237 form a source follower circuit. The MOS transistor 236 is an enable switch which is turned on by activating an enable signal EN, and sets the source follower circuit formed by the MOS transistor 235 and the current source 237 in an operation state.

The charge accumulation portion of the conversion element 210 and the gate of the MOS transistor 235 function as a charge/voltage conversion unit CVC that converts charges accumulated in the charge accumulation portion into a voltage. That is, a voltage V (=Q/C) determined by charges Q accumulated in the charge accumulation portion and a capacitance value C of the charge/voltage conversion unit appears in the charge/voltage conversion unit CVC. The charge/voltage conversion unit CVC is connected to a reset potential Vres via the reset switch 220. When a reset signal PRES is activated, the reset switch 220 is turned on, and the potential of the charge/voltage conversion unit is reset to the reset potential Vres. The reset switch 220 can include a transistor that has the first main electrode (drain) connected to the charge accumulation portion of the conversion element 210, the second main electrode (source) to which the reset potential Vres is applied, and a control electrode (gate). The transistor electrically connects the first main electrode and the second main electrode by receiving an ON voltage at the control electrode, and resets the charge accumulation portion of the conversion element 210.

The clamp circuit 260 clamps, by a clamp capacitor 261, a reset noise level output from the amplifier circuit 230 in accordance with the potential of the reset charge/voltage conversion unit CVC. The clamp circuit 260 is a circuit configured to cancel the reset noise level from a signal (radiation signal) output from the amplifier circuit 230 in accordance with charges (electrical signal) converted by the conversion element 210. The reset noise level includes kTC noise at the time of reset of the charge/voltage conversion unit CVC. A clamp operation is performed by turning on a MOS transistor 262 by activating a clamp signal PCL, and then turning off the MOS transistor 262 by deactivating the clamp signal PCL.

The output side of the clamp capacitor 261 is connected to the gate of a MOS transistor 263. The source of the MOS transistor 263 is connected to a current source 265 via a MOS transistor 264. The MOS transistor 263 and the current source 265 form a source follower circuit. The MOS transistor 264 is an enable switch which is turned on by activating an enable signal ENO supplied to its gate, and sets the source follower circuit formed by the MOS transistor 263 and the current source 265 in an operation state.

The output circuit 310 includes MOS transistors 311, 313, and 315 and row selection switches 312 and 314. The MOS transistors 311, 313, and 315, respectively, form source follower circuits with current sources (not shown) connected to column signal lines 321 and 322.

The sample and hold circuit 280 can sample and hold (hold) a radiation signal as a signal output from the clamp circuit 260 in accordance with charges generated in the conversion element 210. The sample and hold circuit 280 can include a switch 281 and a capacitor 282. The switch 281 is turned on when a sample and hold signal TS is activated by the row selection circuit 120. The radiation signal output from the clamp circuit 260 is written in the capacitor 282 via the switch 281 by activating the sample and hold signal TS.

In the normal mode, in the state in which the reset switch 220 resets the potential of the charge/voltage conversion unit CVC and the MOS transistor 262 is ON, the clamp circuit 260 outputs the noise level (offset component) of the clamp circuit 260. The sample and hold circuit 270 can sample and hold (hold) the noise level of the clamp circuit 260. The sample and hold circuit 270 can include a switch 271 and a capacitor 272. The switch 271 is turned on when a sample and hold signal TN is activated by the row selection circuit 120. A noise level output from the clamp circuit 260 is written in the capacitor 272 via the switch 271 by activating the sample and hold signal TN. In the extension mode, the sample and hold circuit 270 can also be used to hold a radiation signal as a signal output from the clamp circuit 260 in accordance with charges generated in the conversion element 210.

When row selection signals VST are activated, signals corresponding to signals held by the sample and hold circuits 270 and 280 are output to the first column signal line 321 and the second column signal line 322 that form the column signal transmission paths 114. More specifically, a signal N corresponding to a signal (a noise level or a radiation signal) held by the sample and hold circuit 270 is output to the column signal line 321 via the MOS transistor 311 and the row selection switch 312. A signal S corresponding to a signal held by the sample and hold circuit 280 is output to the column signal line 322 via the MOS transistor 313 and the row selection switch 314.

The pixel 112 may include addition switches 301 and 302 configured to add signals of the plurality of pixels 112. In an addition mode, addition mode signals ADDN and ADDS are activated. The capacitors 272 of the plurality of pixels 112 are connected to each other by activating the addition mode signal ADDN, averaging the signals (noise level or radiation signal). The capacitors 282 of the plurality of pixels 112 are connected to each other by activating the addition mode signal ADDS, averaging the radiation signals.

The pixel 112 can include the sensitivity changing unit 240. The sensitivity changing unit 240 can include switches 241 and 242, capacitors 243 and 244, and MOS transistors 245 and 246. When a first change signal WIDE is activated, the switch 241 is turned on, and the capacitance value of the first additional capacitor 243 is added to the capacitance value of the charge/voltage conversion unit CVC. Consequently, the sensitivity of the pixel 112 is decreased. Further, when a second change signal WIDE2 is also activated, the switch 242 is also turned on, and the capacitance value of the second additional capacitor 244 is added to the capacitance value of the charge/voltage conversion unit CVC. Consequently, the sensitivity of the pixel 112 is further decreased. A dynamic range can be widened by adding a function of decreasing the sensitivity of the pixel 112. An enable signal ENW may be activated when the first change signal WIDE is activated. In this case, the MOS transistor 246 performs a source follower operation. Note that when the switch 241 of the sensitivity changing unit 240 is turned on, the potential of the charge accumulation portion of the conversion element 210 may be changed by charge redistribution. Consequently, some signals may be destructed.

The above-described reset signal Pres, enable signal EN, clamp signal PCL, enable signal ENO, sample and hold signals TN and TS, and row selection signals VST are control signals controlled (driven) by the row selection circuit 120 and correspond to the row control signals 122 of FIG. 2. The row selection circuit 120 generates the reset signal Pres, enable signal EN, clamp signal PCL, enable signal ENO, sample and hold signals TN and TS, and row selection signals VST in accordance with the timing signal supplied from the control unit 130.

In the pixel 112 having the arrangement as shown in FIG. 3, signals are not destructed in, for example, the charge accumulation portion of the conversion element 210 in a sample and hold operation. That is, in the pixel 112 having the arrangement as shown in FIG. 3, the radiation signals can be nondestructively read out. Such an arrangement is advantageous to radiation imaging to which the energy subtraction method is applied to be described below.

The extension mode for obtaining a radiation image in accordance with the energy subtraction method will be described below. The extension mode can include the following four sub-modes (extension modes 1, 2, 3, and 4). Here, extension mode 1 is a comparative example, and extension modes 2, 3, and 4 are improved examples of comparative example 1.

Figure 4:
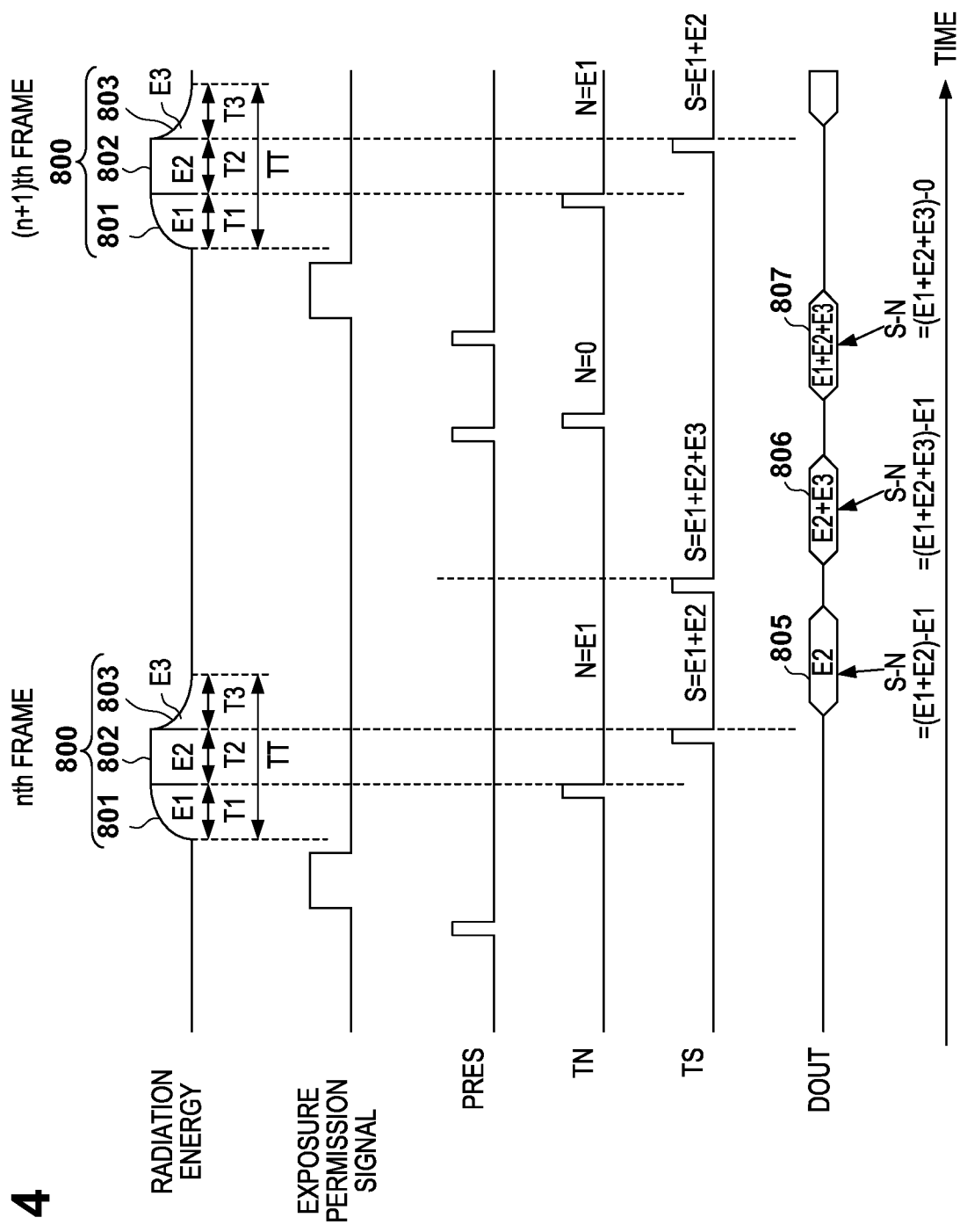
FIG. 4 is a timing chart showing the operation of the radiation imaging apparatus in extension mode 1 (comparative example).

FIG. 4 shows the operation of the radiation imaging apparatus 1 in extension mode 1 (comparative example). In FIG. 4, the abscissa indicates a time. "Radiation energy" is energy of radiation which is emitted from the radiation source 400 and irradiates the imaging unit 100. "PRES" is the reset signal RPES. "TS" is the sample and hold signal TS. "DOUT" is an output of the AD converter 170. The control apparatus 350 that generates an exposure permission signal can control synchronization of radiation emission from the radiation source 400 and the operation of the imaging unit 100. The control unit 130 controls an operation in the imaging unit 100. The clamp signal PCL is also activated over a predetermined period in a period during which the reset signal PRES is activated, and the clamp circuit 260 clamps a noise level.

As shown in the example of FIG. 4, the energy (wavelength) of radiation 800 emitted from the radiation source 400 changes in the radiation period of the radiation. This is caused by the blunt leading and trailing edges of the tube voltage of the radiation source 400. For this reason, assume that the radiation 800 is made from radiation 801 in a leading period, radiation 802 in a stable period, and radiation 803 in a trailing period. Energy E1 of the radiation 801, energy E2 of the radiation 802, and energy E3 of the radiation 803 can be different from each other. By using this, a radiation image according to the energy subtraction method can be obtained.

The control unit 130 defines a first period T1, a second period T2, and a third period T3 such that the first period T1, second period T2, and third period T3 correspond to the leading period, stable period, and trailing period, respectively. Each pixel 112 executes an operation of outputting a first signal corresponding to an electrical signal generated by the conversion element 210 in the first period T1. Further, each pixel 112 executes an operation of outputting a second signal corresponding to an electrical signal generated by the conversion element 210 in the first period T1 and second period T2. Furthermore, each pixel 112 executes an operation of outputting a third signal corresponding to an electrical signal generated by the conversion element 210 in the first period T1, second period T2, and third period T3. The first period T1, second period T2, and third period T3 are periods different from each other. It is planned that radiation having the first energy E1 is emitted in the first period T1, radiation having the second energy E2 is emitted in the second period T2, and radiation having the third energy E3 is emitted in the third period T3.

In extension mode 1, the conversion element 210 of each pixel 112 is not reset (the reset signal Pres is not activated) in an irradiation period TT of the radiation 800. Accordingly, in the irradiation period TT of the radiation 800, an electrical signal (charges) corresponding to the incident radiation is kept accumulated in the conversion element 210. In the irradiation period TT of the radiation 800, since the conversion element 210 of each pixel 112 is not reset, it is advantageous in reducing the irradiation of the radiation which does not contribute to the imaging and obtaining a radiation image for the energy subtraction method within a shorter time.

Before emission (irradiation for the imaging unit 100) of the radiation 800, the reset signal PRES is activated for a predetermined period and accordingly the conversion element 210 is reset. At this time, the clamp signal PCL is also activated for the predetermined period, and the clamp circuit 260 is clamped to the reset level (the noise level).

After the reset signal PRES is activated for the predetermined period, an exposure permission signal is transmitted from the exposure control apparatus 300 to the radiation source 400, and the radiation is emitted from the radiation source 400 in response to the exposure permission signal. When the predetermined period has elapsed upon activation of the reset signal PRES for the predetermined period, the sample and hold signal TN is activated for the predetermined period. Accordingly, upon reception of irradiation of the radiation 801 having the energy E1, a signal (E1) corresponding to an electrical signal generated by the conversion element 210 of the pixel 112 of the pixel array 110 is sampled and held by the sample and hold circuit 270.

When the predetermined period has elapsed upon activation of the sample and hold signal TN for the predetermined period, the sample and hold signal TS is activated for the predetermined period. Accordingly, upon reception of irradiation of the radiation 801 having the energy E1 and the radiation 802 having the energy E2, a signal (E1+E2) corresponding to an electrical signal generated by the conversion element 210 of the pixel 112 of the pixel array 110 is sampled and held by the sample and hold circuit 280.

Next, a signal corresponding to the difference between the signal (E1) sampled and held by the sample and hold circuit 270 and the signal (E1+E2) sampled and held by the sample and hold circuit 280 is output from the readout circuit RC as a first signal 805. Referring to FIG. 4, "N" indicates a signal sampled and held by the sample and hold circuit 270 and output to the first column signal line 321, and "S" indicates a signal sampled and held by the sample and hold circuit 280 and output to the second column signal line 322.

When the predetermined period has elapsed upon activation of the sample and hold signal TS for the predetermined period (upon completion of irradiation (irradiation of the radiation 800) of the radiation 803 having the energy E3), the sample and hold signal TS is activated for the predetermined period again. Accordingly, upon reception of irradiation of the radiation 801 having the energy E1, the radiation 802 having the energy E2, and the radiation 803 having the energy E3, a signal (E1+E2+E3) corresponding to an electrical signal generated by the conversion element 210 of the pixel 112 of the pixel array 110 is sampled and held by the sample and hold circuit 280.

Next, a signal corresponding to the difference between the signal (E1) sampled and held by the sample and hold circuit 270 and the signal (E1+E2+E3) sampled and held by the sample and hold circuit 280 is output from the readout circuit RC as a second signal 806.

Next, the reset signal PRES is activated for the predetermined period, and then the sample and hold signal TN is activated for the predetermined period. Accordingly, the reset level (0) is sampled and held by the sample and hold circuit 270. Next, a signal corresponding to the difference between the signal (0) sampled and held by the sample and hold circuit 270 and the signal (E1+E2+E3) sampled and held by the sample and hold circuit 280 is output from the readout circuit RC as a third signal 807.

By repeating the above operation a plurality of times, radiation images of a plurality of frames (that is, a moving image) can be obtained.

The signal processing unit 352 can obtain the first signal 805 (E2), the second signal 806 (E2+E3), and the third signal 807 (E1+E2+E3) as described above. The signal processing unit 352 can obtain an irradiation amount e1 of the radiation 801 having the energy E1, an irradiation amount e2 of the radiation 802 having the energy E2, and an irradiation amount e3 of the radiation 803 having the energy E3 based on the first signal 805, the second signal 806, and the third signal 807. More specifically, the signal processing unit 352 calculates a difference ((E2+E3)–E2) between the first signal 805 (E2) and the second signal (E2+E3) to obtain the irradiation amount e3 of the radiation 803 having the energy E3. The signal processing unit 352 calculates a difference ((E1+E2+E3)–(E2+E3)) between the second signal 806 (E2+E3) and the third signal (E1+E2+E3) to obtain the irradiation amount e1 of the radiation 801 having the energy E1. The first signal 805 (E2) indicates the irradiation amount e2 of the radiation 802 having the energy E2.

Therefore, the signal processing unit 352 can obtain the radiation image by the energy subtraction method based on the irradiation amount e1 of the radiation 801 having the energy E1, the irradiation amount e2 of the radiation 802 having the energy E2, and the irradiation amount e3 of the radiation 803 having the energy E3. The energy subtraction method can be selected from various methods. For example, it is possible, by calculating a difference between the radiation image of the first energy and the radiation image of the second energy, to obtain a bone image and a soft tissue image. The bone image and the soft tissue image may be generated by solving nonlinear simultaneous equations based on the radiation image of the first energy and the radiation image of the second energy. It is also possible to obtain a contrast medium image and the soft tissue image based on the radiation image of the first energy and the radiation image of the second energy. It is also possible to obtain an electron density image and an effective atomic number image based on the radiation image of the first energy and the radiation image of the second energy.

Figure 5:
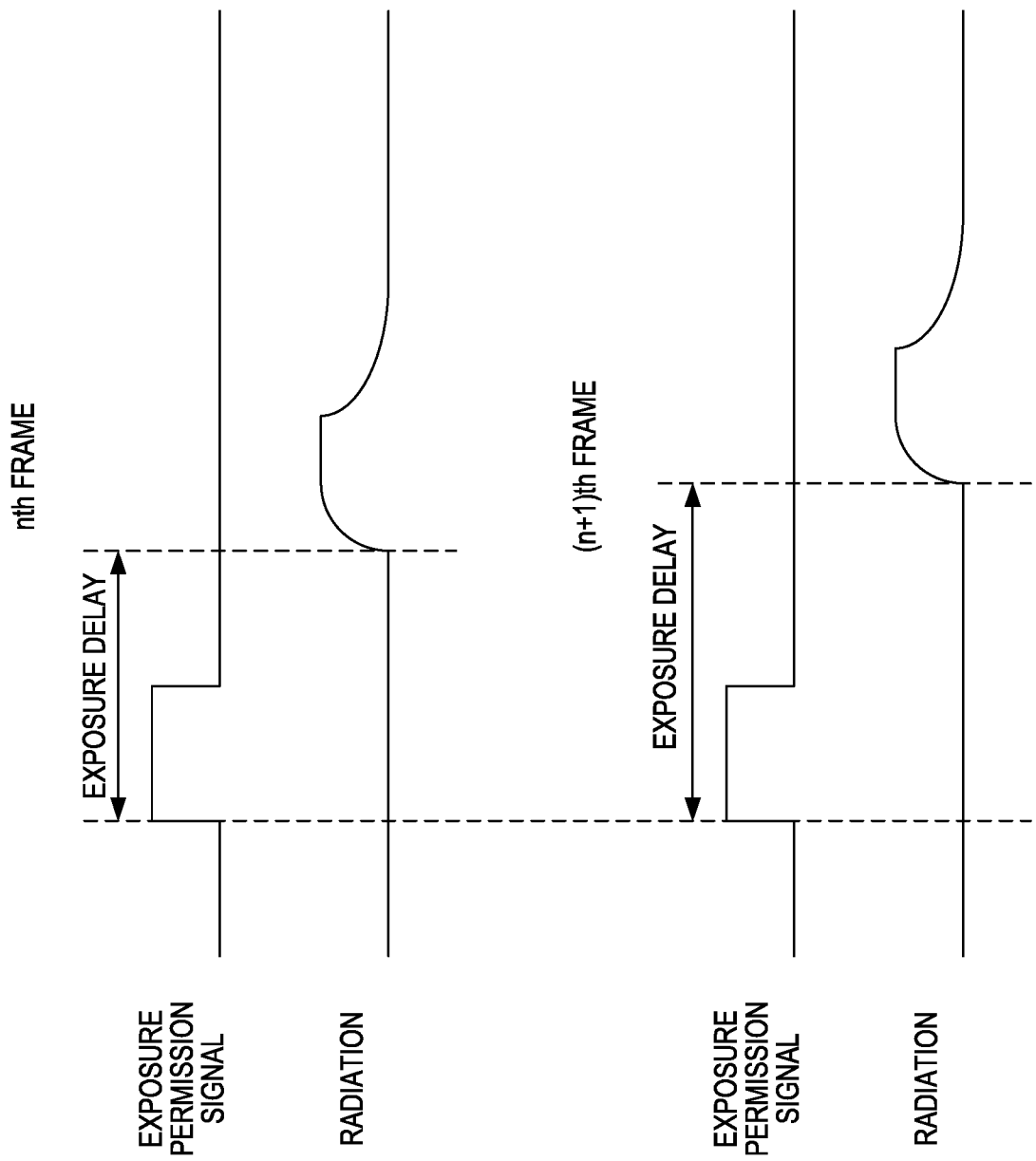
FIG. 5 is a view for explaining a problem in extension mode 1 (comparative example).

The problem in extension mode 1 (comparative example) will be described with reference to FIG. 5. As shown in the example of FIG. 5, the time (to be referred to as "exposure delay") from the transmission of an exposure permission signal to the exposure control apparatus 300 by the control apparatus 350 to the start of radiation irradiation (exposure) by the radiation source 400 can be different for each frame. In the example shown in FIG. 5, the exposure delay in the (n+1)th frame is larger than the exposure delay in the nth frame.

When explained with reference to FIG. 4, the fact that the exposure delay is different for each frame means that the periods T1 and T2 from the start of irradiation of the radiation 800 to the completion of the sampling and holding of the sample and hold circuits 270 and 280, respectively, vary. Therefore, the energy and irradiation amount (dose) of the radiation detected as each of the first signal 805, the second signal 806, and the third signal 807 can change between the frames. This means that the energy and irradiation amount (dose) of the radiation detected as each of the irradiation amount e1, the irradiation amount e2, and the irradiation amount e3 change between the frames, so that the accuracy of energy subtraction based on the irradiation amount e1, the irradiation amount e2, and the irradiation amount e3 can be decreased. This can cause an artifact and/or blinking in the moving image.

Figure 6:
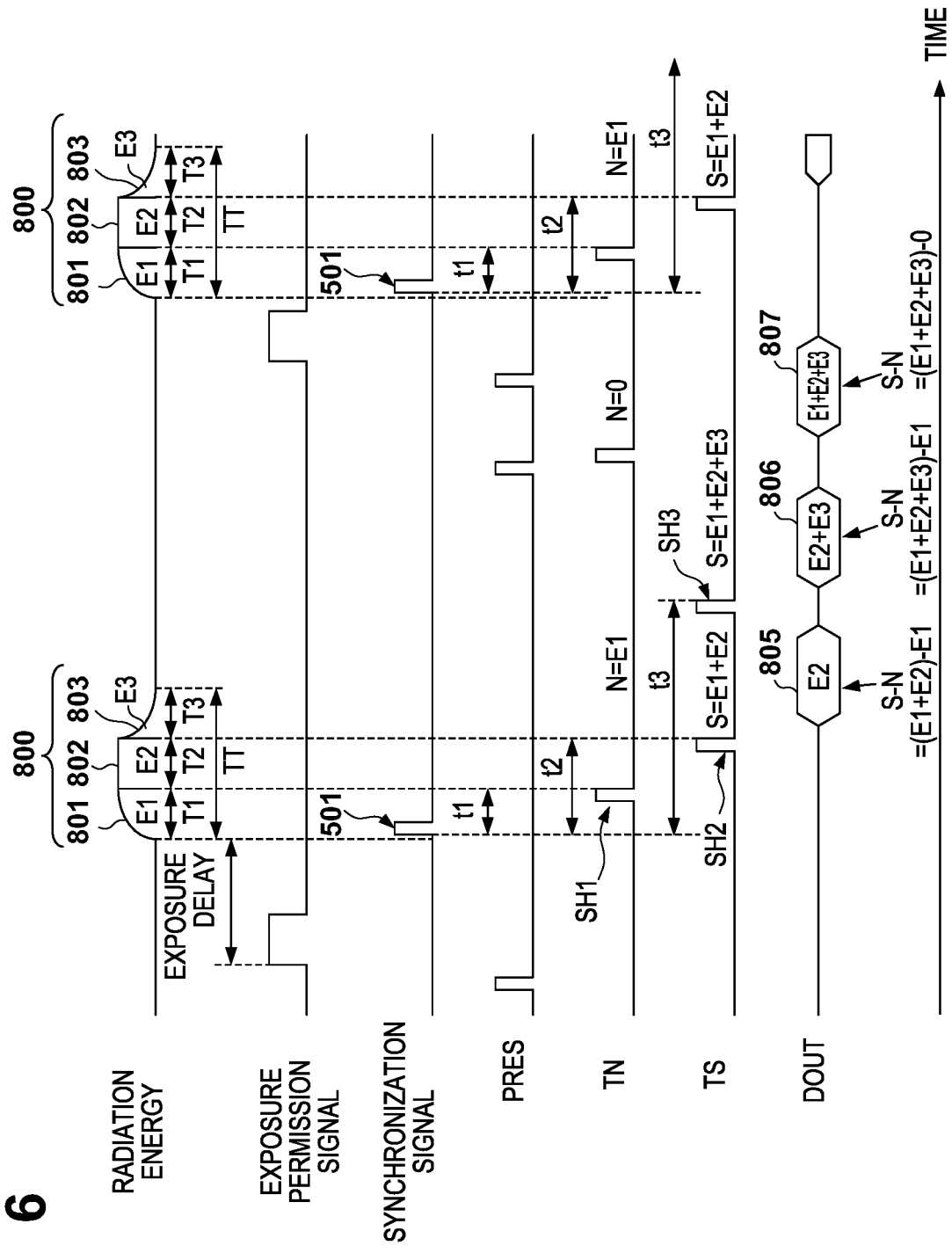
FIG. 6 is a timing chart showing the operation of the radiation imaging apparatus in extension mode 2.

FIG. 6 shows the operation of the radiation imaging apparatus 1 in extension mode 2. Matters not mentioned as extension mode 2 can follow extension mode 1. In order to solve the problem in extension mode 1 (comparative example), it is required to cause the sample and hold circuits 270 and 280 of the pixel 112 to perform sampling and holding in synchronization with the radiation actually emitted from the radiation source 400 instead of the exposure permission signal. Each time a synchronization signal 501 is supplied from the detection unit 190, the control unit 130 determines the timing of each of a plurality of sample and hold operations SH1, SH2, and SH3 in each of the plurality of pixels 112 of the pixel array 110. In other words, each time the start of radiation irradiation is detected by the detection unit 190, the control unit 130 determines the timing of each of the plurality of sample and hold operations SH1, SH2, and SH3 in each of the plurality of pixels 112 of the pixel array 110. During the period between the first sample and hold operation SH1 of the plurality of sample and hold operations SH1, SH2, and SH3 and the last sample and hold operation of the plurality of sample and hold operations SH1, SH2, and SH3, the reset switch 220 does not reset the conversion element 210.

Here, in order to obtain a radiation image by the energy subtraction method, the timing of at least one sample and hold operation of the plurality of sample and hold operations SH1, SH2, and SH3 is a timing in the radiation irradiation period TT. In the first embodiment, the timings of the two sample and hold operations SH1 and SH2 of the three sample and hold operations SH1, SH2, and SH3 are timings in the radiation irradiation period TT. The timings of the plurality of sample and hold operations SH1, SH2, and SH3 can be determined in accordance with elapsed times t1, t2, and t3 from the synchronization signal, respectively. Therefore, the period from the start of radiation irradiation to the end of the sample and hold operation SH1 is made constant between frames. Further, the period from the start of radiation irradiation to the end of the sample and hold operation SH2 is made constant between frames. Furthermore, the period from the start of radiation irradiation to the end of the sample and hold operation SH3 is made constant between frames. This can suppress a decrease in accuracy of the energy subtraction, and reduce an artifact and/or blinking in a moving image.

Figure 7:
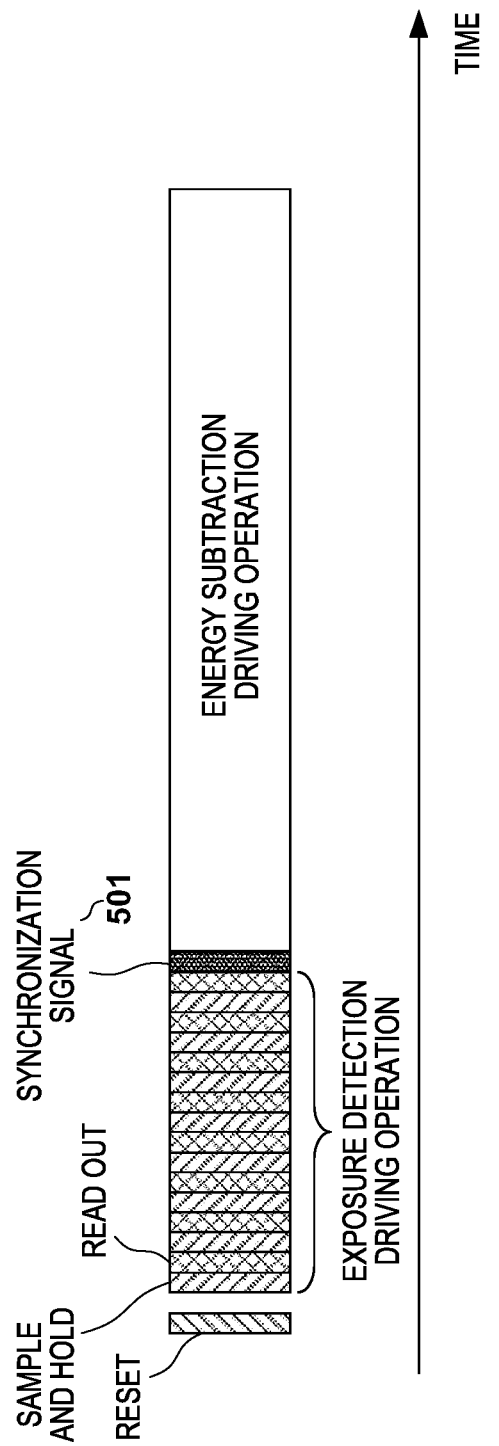
FIG. 7 is a view showing a method of detecting, by a detection unit, the start of irradiation of radiation from a radiation source.

FIG. 7 exemplarily shows a method of detecting, by the detection unit 190, the start of irradiation of radiation from the radiation source 400. The reset switch 220 is turned on by activating the reset signal PRES. After the "reset" of the charge accumulation portion of the conversion element 210, an exposure detection driving operation is performed. If the start of radiation irradiation is detected in the exposure detection driving operation, the process transitions to an energy subtraction driving operation. The exposure detection driving operation includes repetition of "sampling and holding" by the sample and hold circuits 270 and 280 of the pixel 112 and "reading out" of the signal from the pixel 112 by the readout circuit RC. The exposure detection driving operation and the energy subtraction driving operation are controlled by the control unit 130. When the signal read out from the pixel 112 by the readout circuit RC exceeds a threshold value, the detection unit 190 determines that radiation irradiation by the radiation source 400 has been started, and generates the synchronization signal 501. In response to this, the control unit 130 starts the energy subtraction driving operation. The energy subtraction driving operation includes driving in response to the synchronization signal 501 shown in FIG. 6, that is, the plurality of sample and hold operations SH1, SH2, and SH3 by the sample and hold circuits 270 and 280 of each of the plurality of pixels 112 and a readout operation by the readout circuit RC. Here, the readout operation by the readout circuit RC includes an operation of outputting the first signal 805, the second signal 806, and the third signal 807.

The repetition of "sampling and holding" and "reading out" in the exposure detection driving operation is preferably performed at a high speed (for example, µs order). This is because the timing at which the start of radiation irradiation is detected is delayed by the time required for "sampling and holding" and "reading out". In order to increase the speed, binning (the number of pixels added) during the reading out may be changed during the period of the exposure detection driving operation. As the number of pixels added increases as binning of 2×2, 4×4, 8×8, . . . , the readout time can be shortened. Since the image obtained by reading out in the exposure detection driving operation is used to determine presence/absence of X-ray exposure for determining the start of radiation irradiation, it is not necessary to consider the resolution. Therefore, the resolution may be greatly reduced such as 32×32 binning to shorten the time required for reading out. Further, the number of pixels 112 to be read out may be limited. For example, in order to read out the signals from the pixels in some rows, the other rows may be skipped.

When the detection unit 190 outputs the synchronization signal 501, the process transitions from the exposure detection operation to the energy subtraction driving operation, so that settings for binning and the like are changed to those for the energy subtraction driving operation. At this time, the sample and hold circuit 270 may be or may not be reset.

In an example different from the above, the synchronization signal 501 is generated in response to the signal read out from the pixel array 110 by the readout circuit RC exceeding a first threshold value, and the timing of the sample and hold operation SH1 can be determined accordingly. Thereafter, the timing of the sample and hold operation SH2 can be determined in response to the signal read out from the pixel array 110 by the readout circuit RC exceeding a second threshold value. Further, the timing of the sample and hold operation SH3 can be determined in response to the signal read out from the pixel array 110 by the readout circuit RC exceeding a third threshold value.

Figure 8:
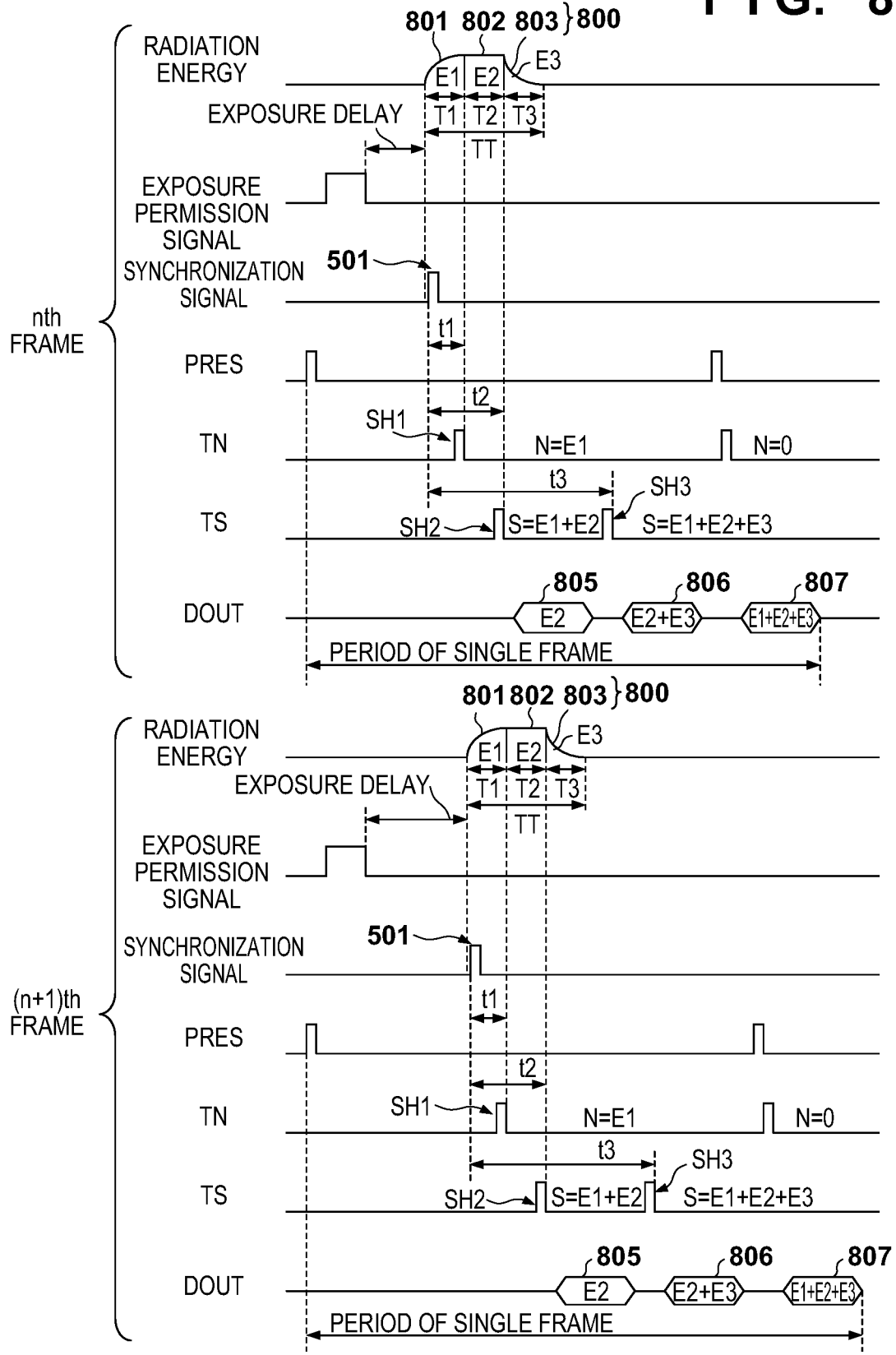
FIG. 8 is a timing chart for explaining a frame rate in extension mode 2.

As shown in FIG. 8, in extension mode 2, since the frame period is determined in accordance with the exposure delay, the frame period can be different between frames. In addition, in extension mode 2, the period from the activation of the reset signal PRES to the start of radiation irradiation depends on the exposure delay. This means that the noise level accumulated in the conversion element 210 from the activation of the reset signal PRES to the start of radiation irradiation depends on the exposure delay. Therefore, in extension mode 2, the noise level can be different between frames.

Figure 9:
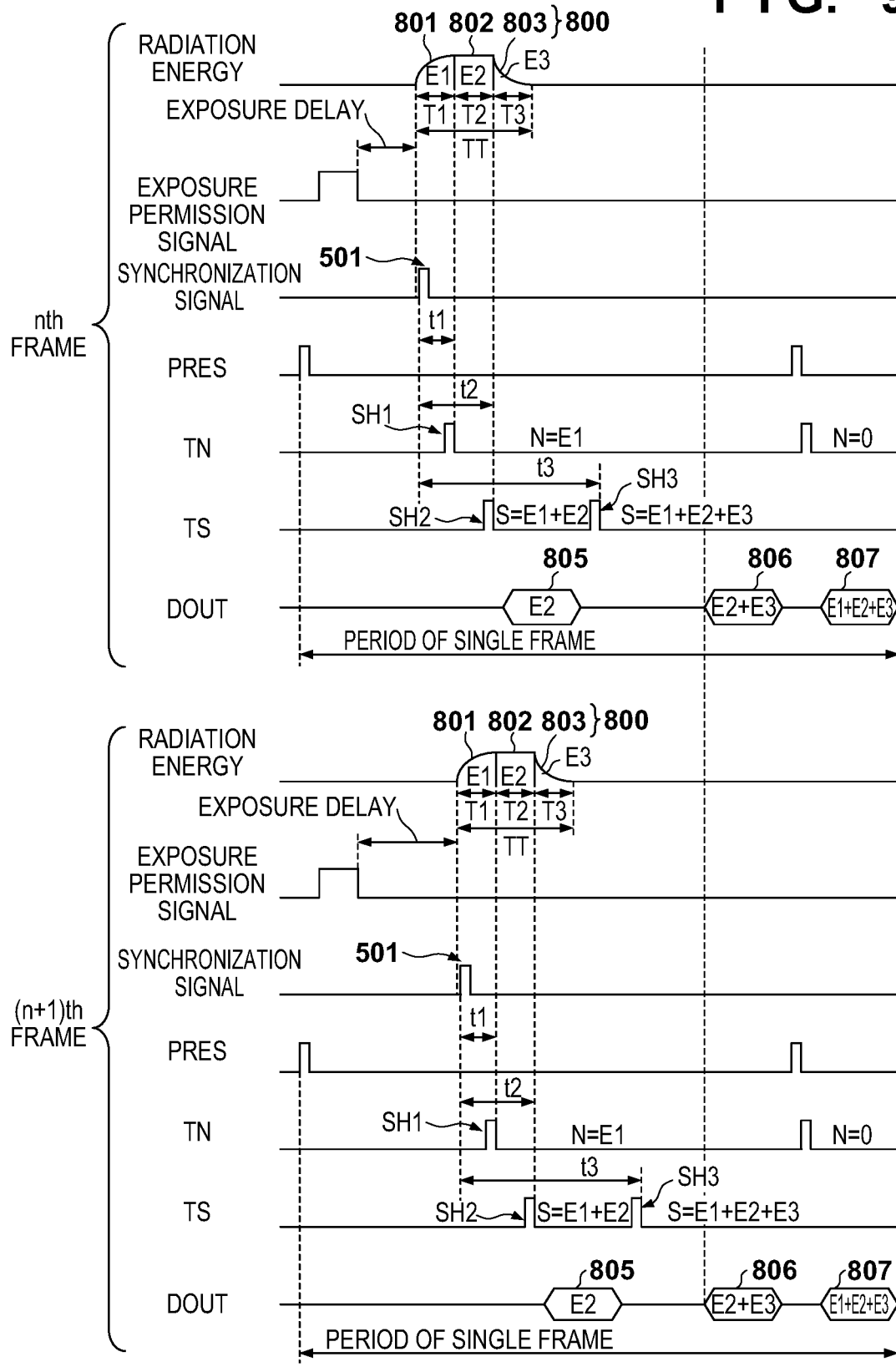
FIG. 9 is a timing chart showing the operation of the radiation imaging apparatus in extension mode 3.

FIG. 9 shows the operation of the radiation imaging apparatus 1 in extension mode 3. Matters not mentioned as extension mode 3 can follow extension mode 1. Extension mode 3 is a mode in which the problem in extension mode 2, that is, the problem that the frame period can be different between frames has been solved. In extension mode 3, the frame rate is constant without depending on the exposure delay. In extension mode 3, the control unit 130 controls the readout circuit RC such that the timing at which the output of the third signal 807 is completed is common between frames. For example, the control unit 130 controls the timing at which the readout circuit RC starts reading out the second signal 806, or controls the drive timing of the readout circuit RC so as to make the timing at which the readout circuit RC starts reading out the second signal 806 constant between frames. Accordingly, the timing at which the output of the third signal 807 is completed can be made constant between frames.

Instead of the above method, the control unit 130 may make the frame rate constant by adjusting the time from the completion of reading out of the third signal 807 to the timing at which the next frame starts (for example, the timing at which the reset signal PRES is activated).

Also in extension mode 3, the reset switch 220 does not reset the conversion element 210 during the period between the first sample and hold operation SH1 and the last sample and hold operation SH3 of the plurality of sample and hold operations SH1, SH2, and SH3.

Figure 10:
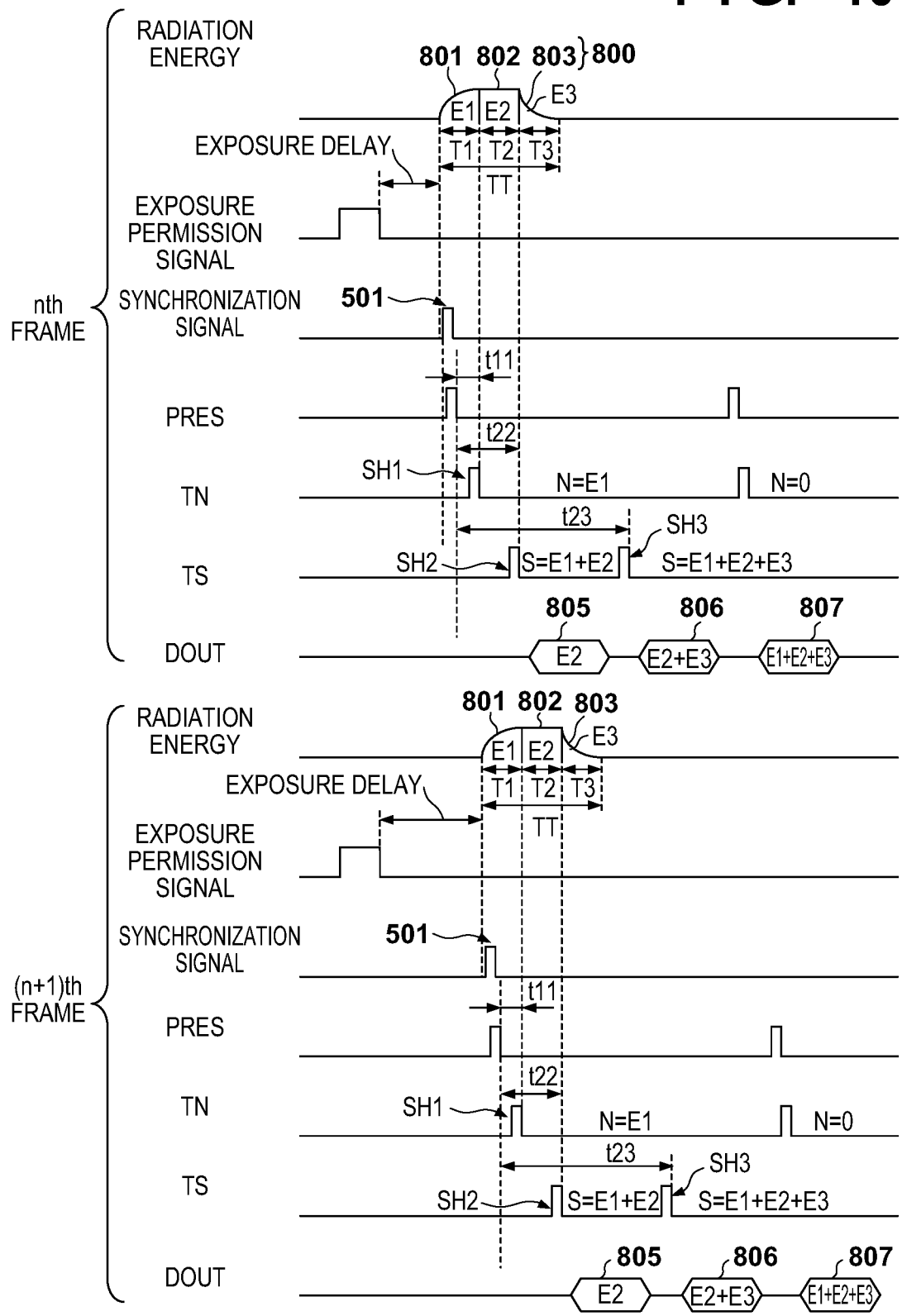
FIG. 10 is a timing chart showing the operation of the radiation imaging apparatus in extension mode 4.

FIG. 10 shows the operation of the radiation imaging apparatus 1 in extension mode 4. Matters not mentioned as extension mode 4 can follow extension mode 1. In extension mode 4, the accumulation time from the activation of the reset signal PRES to the end of the sample and hold operation SH1 is constant between frames. Further, in extension mode 4, the accumulation time from the activation of the reset signal PRES to the end of the sample and hold operation SH2 is constant between frames. Furthermore, in extension mode 4, the accumulation time from the activation of the reset signal PRES to the end of the sample and hold operation SH3 is constant between frames. Therefore, the noise level accumulated in the conversion element 210 is constant between frames without depending on the exposure delay. Note that the frame rate is not constant in extension mode 4 described above, but the frame rate may be made constant in extension mode 4 as in extension mode 3.

Also in extension mode 4, the reset switch 220 does not reset the conversion element 210 during the period between the first sample and hold operation SH1 and the last sample and hold operation SH3 of the plurality of sample and hold operations SH1, SH2, and SH3.

In the above description, the embodiment in which three types of images having different energies are obtained has been described. However, the present invention is not limited to such an embodiment. For example, four types of images having different energies may be obtained by increasing the number of sample and hold operations. Alternatively, two types of images having different energies may be obtained by decreasing the number of sample and hold operations. Alternatively, two types of images having different energies may be obtained from three types of images having different energies.

In the above example, a plurality of images having different energies are obtained by using the blunt leading and trailing edges of the tube voltage of the radiation source 400, and a new radiation image is formed based on the plurality of images. The plurality of images having different energies can be obtained by intentionally adjusting the waveform of the tube voltage of the radiation source 400. Alternatively, the plurality of images may be obtained by emitting radiation having a wide energy band (wavelength band) from the radiation source 400 and changing the energy of the radiation by changing a plurality of filters.

In the first embodiment, the detection unit 190 detects the start of radiation irradiation by the radiation source 400 based on the radiation emitted from the radiation source 400. In the second and third embodiments to be described below, a detection unit 190 detects the start of radiation irradiation by a radiation source 400 based on information provided from the radiation source 400. That is, the detection unit 190 can be configured to detect the start of radiation irradiation by the radiation source 400 based on the radiation emitted from the radiation source 400 or information provided from the radiation source 400.

Figure 11:
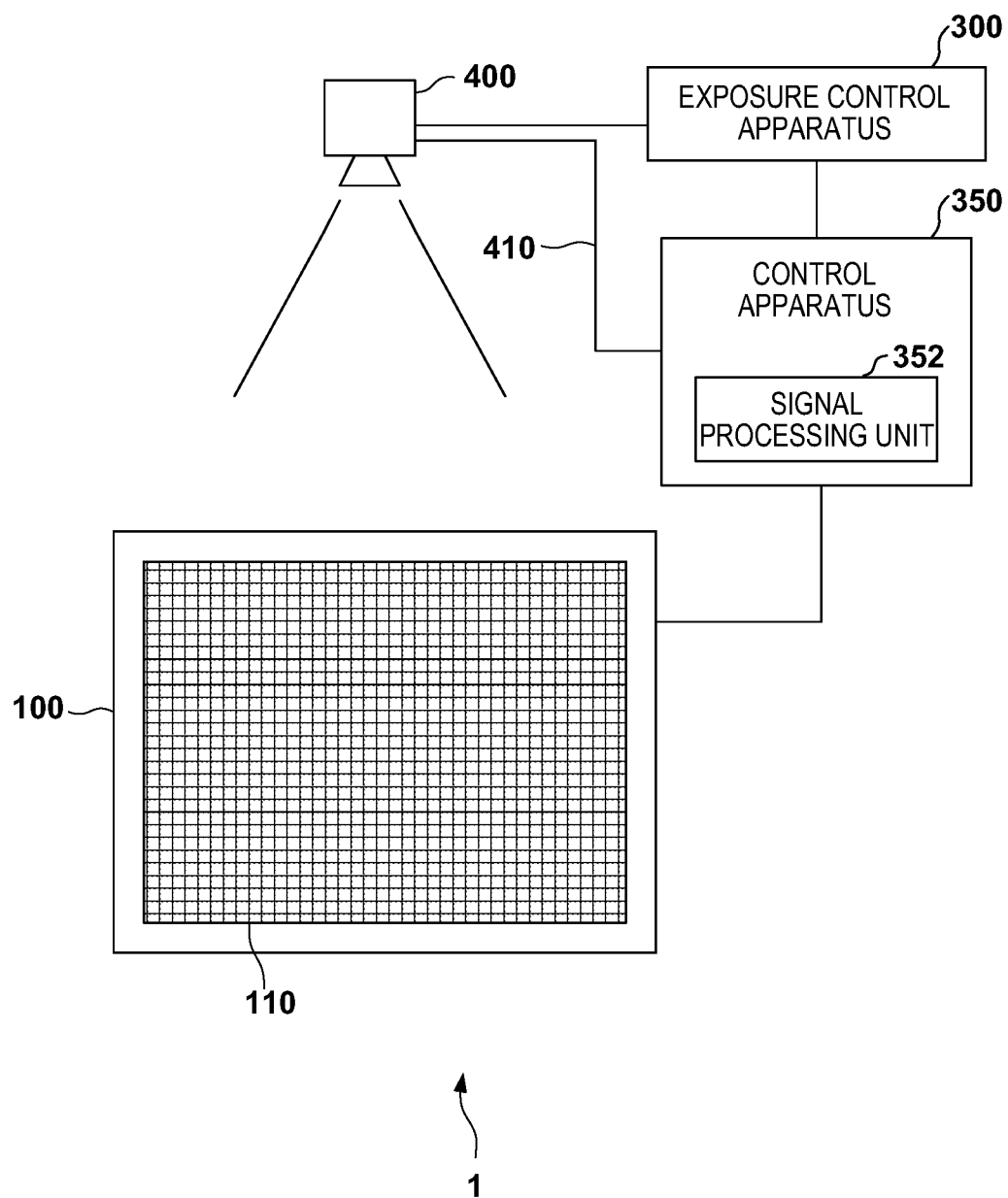
FIG. 11 is a diagram showing the arrangement of a radiation imaging apparatus according to the second embodiment of the present invention.

FIG. 11 shows the arrangement of a radiation imaging apparatus 1 according to the second embodiment of the present invention. Matters not mentioned as the second embodiment can follow the first embodiment. In the second embodiment, the radiation source 400 provides driving current information indicating a driving current for generating radiation to a control apparatus 350 via a monitor line 410, for example. The radiation source 400 may be configured to provide the driving current information to the control apparatus 350 via an exposure control apparatus 300. The driving current is a current that flows between the cathode and the anode of the radiation source 400, and can be detected by an ammeter incorporated in the radiation source 400. For example, the detection unit 190 may be provided in the control apparatus 350, provided in an imaging unit 100, or provided separately from the control apparatus 350 and the imaging unit 100. When the detection unit 190 is provided in the imaging unit 100, the driving current information can be provided from the radiation source 400 to the detection unit 190 via the control apparatus 350 or directly. The detection unit 190 can detect the start of radiation irradiation by the radiation source 400 and generate a synchronization signal 501 when a value indicated by information such as the driving current information provided from the radiation source 400 exceeds a threshold value.

Figure 12:
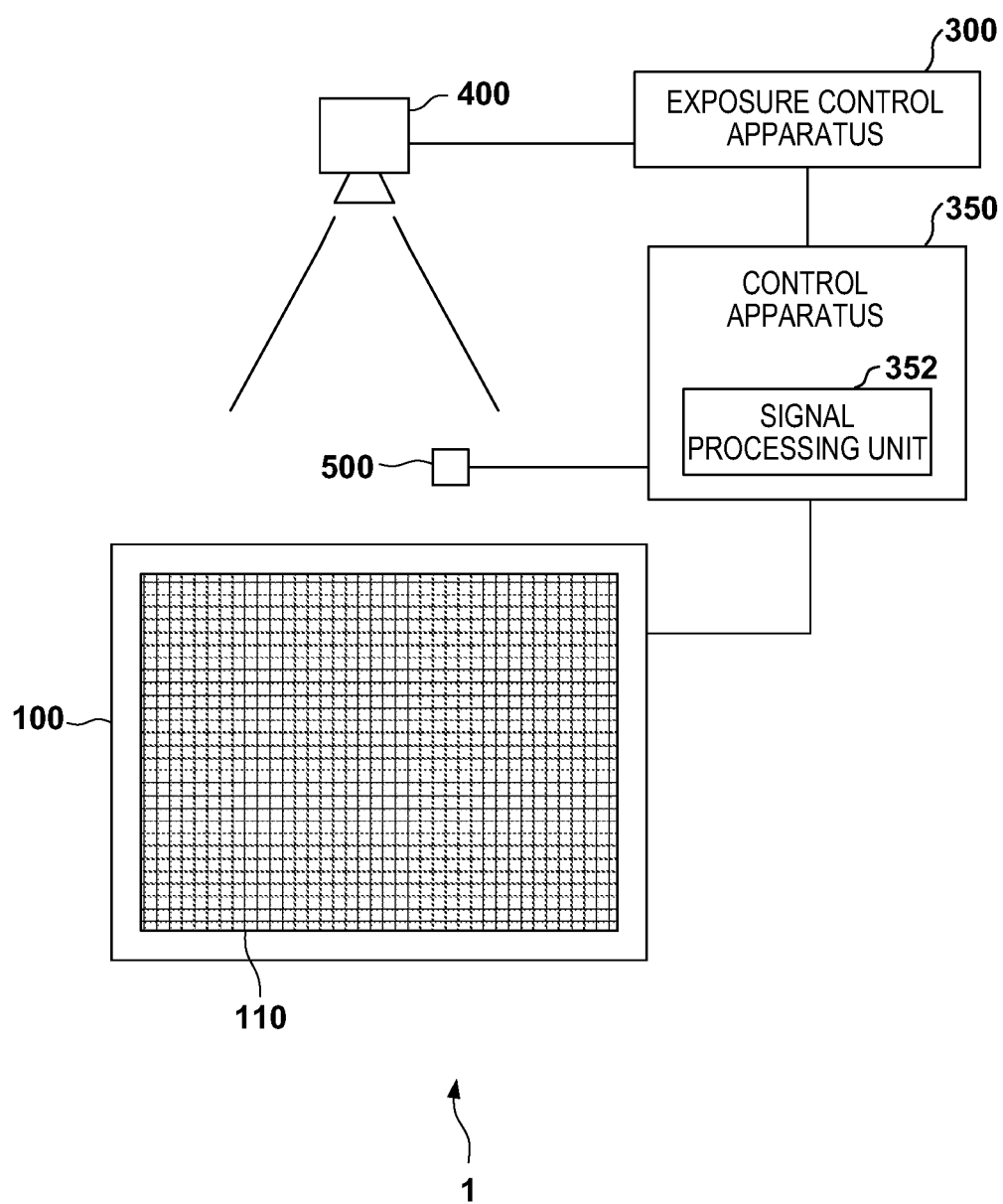
FIG. 12 is a diagram showing the arrangement of a radiation imaging apparatus according to the third embodiment of the present invention.

FIG. 12 shows the arrangement of a radiation imaging apparatus 1 according to the third embodiment of the present invention. Matters not mentioned as the third embodiment can follow the first embodiment. The radiation imaging apparatus 1 according to the third embodiment includes a radiation detection sensor 500 provided separately from a pixel array 110. The radiation detection sensor 500 may be arranged in an imaging unit 100 or may be arranged in a path between a radiation source 400 and the imaging unit 100. A detection unit 190 detects the start of radiation irradiation by the radiation source 400 based on the output from the radiation detection sensor 500, and generates a synchronization signal 501.

The radiation detection sensor 500 may have energy resolution. In this case, the detection unit 190 can be configured to detect the start of radiation irradiation by the radiation source 400 based on the energy of the radiation detected by the radiation detection sensor 500. According to such an arrangement, a radiation image can be stably obtained even when the leading edge of the energy of the radiation emitted by the radiation source 400 varies or when the pulse width of the energy varies.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising:
a pixel array including a plurality of pixels, each of the plurality of pixels including a converter configured to convert radiation into an electrical signal, and a sample and hold circuit configured to sample and hold the electric signal from the conversion element;
a readout circuit configured to read out signals from the pixel array;
a detector configured to detect a start of irradiation of radiation by a radiation source based on radiation emitted from the radiation source or information provided from the radiation source; and
a controller configured to determine a timing of each of a plurality of sample and hold operations by the sample and hold circuit in each of the plurality of pixels each time the start of irradiation of radiation is detected by the detector, wherein
the timing of at least one sample and hold operation of the plurality of sample and hold operations is a timing in a radiation irradiation period, and
the controller determines the timing of each of the plurality of sample and hold operations such that radiation images having different energies can be obtained.

2. The radiation imaging apparatus according to claim 1, wherein each of the plurality of pixels further includes a resetter configured to reset the converter, and
in each of the plurality of pixels, the resetter does not reset the converter in a period between the first and last of the plurality of sample and hold operations.

3. The radiation imaging apparatus according to claim 2, wherein the controller controls the plurality of pixels such that accumulation times in the plurality of pixels are made constant between a plurality of frames.

4. The radiation imaging apparatus according to claim 1, wherein the detector detects a start of irradiation of radiation by the radiation source based on an electrical signal obtained from the pixel array.

5. The radiation imaging apparatus according to claim 1, wherein the detector detects a start of irradiation of radiation by the radiation source based on a driving current for generating radiation in the radiation source.

6. The radiation imaging apparatus according to claim 1, further comprising a radiation detection sensor provided separately from the pixel array, wherein
the detector detects a start of irradiation of radiation by the radiation source based on an output from the radiation detection sensor.

7. The radiation imaging apparatus according to claim 6, wherein the radiation detection sensor has energy resolution, and
the detection unit detects a start of irradiation of radiation by the radiation source based on an energy of radiation detected by the radiation detection sensor.

8. The radiation imaging apparatus according to claim 1, wherein the controller controls the plurality of pixels so as to make a frame rate constant.

9. The radiation imaging apparatus according to claim 1, further comprising a control apparatus configured to transmit an exposure permission signal to an exposure control apparatus configured to control the radiation source, wherein
the radiation source emits radiation in accordance with the exposure permission signal.

10. A radiation imaging apparatus, comprising:
a pixel array including a plurality of pixels arrayed to form a plurality of rows and a plurality of columns, each of the plurality of pixels including a converter configured to convert radiation into an electrical signal, and a sample and hold circuit configured to sample and hold the electric signal from the converter;
a readout circuit configured to read out signals from the sample and hold circuit in each of the plurality of pixels;
a detector configured to detect an event when (i) a signal obtained from the pixel array exceeds a threshold value assigned thereto, (ii) an output from a radiation detection sensor provided separately from the pixel array exceeds a threshold value assigned thereto, or (iii) information provided from the radiation source exceeds a threshold value assigned thereto; and
a controller configured to determine a timing of each of a plurality of sample and hold operations by the sample and hold circuit in each of the plurality of pixels each time the event is detected by the detector, wherein
the timing of at least one sample and hold operation of the plurality of sample and hold operations is performed in a radiation irradiation period, and
the controller determines a timing of each of the plurality of sample and hold operations such that radiation images having different energies can be obtained.

11. The radiation imaging apparatus according to claim 10, wherein each of the plurality of pixels further includes a resetter configured to reset the converter, and
in each of the plurality of pixels, the resetter does not reset the converter in a period between the first and last of the plurality of sample and hold operations.

12. The radiation imaging apparatus according to claim 11, wherein the information provided from the radiation source is a driving current for generating radiation in the radiation source.

13. The radiation imaging apparatus according to claim 11, wherein the controller controls the readout circuit so as to make a frame rate constant.

14. The radiation imaging apparatus according to claim 11, wherein the controller controls the sample and hold circuit and the resetter of the plurality of pixels such that accumulation times in the plurality of pixel are made constant between a plurality of frames.

15. The radiation imaging apparatus according to claim 10, further comprising a control apparatus configured to transmit an exposure permission signal to an exposure control apparatus configured to control the radiation source, wherein
the radiation source emits radiation in accordance with the exposure permission signal.

16. The radiation imaging apparatus according to claim 10, wherein the detector is further configured to detect events when (iv) the signal obtained from the pixel array exceeds respective threshold values assigned thereto, (v) the output from the radiation detection sensor exceeds respective threshold values assigned thereto, or (vi) information provided from the radiation source exceeds respective threshold values assigned thereto, and
the controller is configured to determine timings of respective ones of the plurality of sample and hold operations based on the respective events detected by the detector.

* * * * *